(12) United States Patent
Ghadiri et al.

(10) Patent No.: US 6,905,878 B2
(45) Date of Patent: Jun. 14, 2005

(54) DNA ARRAY FOR HIGH THROUGHPUT SOLID-PHASE TRANSFECTION AND METHOD FOR PRODUCING THE SAME

(75) Inventors: M. Reza Ghadiri, San Diego, CA (US); Masato Miyake, Amagasaki (JP)

(73) Assignee: The Scripps Research Institute, La Jolla, CA (US)

( * ) Notice: Subject to any disclaimer, the term of this patent is extended or adjusted under 35 U.S.C. 154(b) by 66 days.

(21) Appl. No.: 10/324,780

(22) Filed: Dec. 19, 2002

(65) Prior Publication Data

US 2004/0121333 A1 Jun. 24, 2004

(51) Int. Cl.⁷ .............................................. C12N 15/88
(52) U.S. Cl. .................... 435/458; 435/320.1
(58) Field of Search ............................... 435/320.1, 458

(56) References Cited

PUBLICATIONS

Ziauddin et al., Nature, vol. 411, May 3, 2001, pp. 107–110.*

* cited by examiner

*Primary Examiner*—James Ketter
(74) *Attorney, Agent, or Firm*—Thomas Fitting; Michael J. McCarthy (57) ABSTRACT

The present invention relates to a DNA array for high throughput and highly efficient solid-based transfection which comprises a plurality of dried spots on a solid support, said dried spot comprises (1) a plasmid DNA to be introduced into cells, (2) a transfection reagent and (3) a cell-adhesion protein and to a high throughput and highly efficient solid-based transfection method to introduce plasmid DNA into cells, using the same.

20 Claims, 6 Drawing Sheets

DNA ARRAY FOR HIGH THROUGHPUT SOLID-PHASE TRANSFECTION AND METHOD FOR PRODUCING THE SAME

TECHNICAL FIELD

This invention relates to a DNA array for high throughput solid-phase transfection system, a method for producing the DNA array, reagents to be used for producing the DNA array, and a method for carrying out solid-phase high throughput transfection using the DNA array.

BACKGROUND ART

Hitherto, liquid-phase based transfection system has been used for introduction of DNA into mammalian cells. The following methods have been used for transfection of mammalian cells so far.
(1) Calcium phosphate coprecipitation method (Chen, C. and Okayama, H.: Biotech., 6, 632–638, 1988),
(2) Lipofection-mediated transfer method (Rabindran S. K. et. al.: Science 259, 230–234, 1993),
(3) DEAE dextran-mediated transfer method (Sussman, D. J. and Milman, G.: Mol. Cell. Biol., 4, 1641–1643, 1984),
(4) Electroporation method (Chu, G. et. al.: Nuc. Acid. Res., 15, 1311–1326, 1987), and
(5) Microinjection method (Graessmann, M. and Graessmann A.: Proc. Natl. Acad. Sci. USA, 73, 366–370, 1976).

The above mentioned methods (1) to (4) need $10^4$ to $10^6$ cells as well as 0.1 to 10 $\mu$g DNA, in which the transfection efficiency is the maximal level of about 20%, although it is difficult to maintain the maximal transfection efficiency under various conditions. Especially, transfection efficiencies are variable depending on cell types and these transfection procedures are complicated and time-consuming. Under these circumstances, it is almost impossible to establish a high throughput transfection method by miniaturization and automation of the above mentioned transfection systems (1) to (4). In the meanwhile, the above mentioned method (5) requires much lesser amount of cells and DNA for transfection than the above mentioned methods (1) to (4), however, the procedure requires a high level of skill and a long-term experience since microinjection of DNA into cells is directly carried out under an observation with a microscope. Therefore, a liquid-phase transfection system is not suitable for high throughput transfection.

At present, a high throughput transfection system is highly required as shown in the following example: When cell proliferation is initiated by addition of various stimulations, the successive signal transductions are controlled by networks of interacting proteins.

Signal transduction and processing generally take place through specific protein-protein interactions mediated by protein structural transition and/or chemical transformations. Because of the complexity and our present incomplete understanding of protein circuitry and network dynamics and function, correlating a particular phenotype to a set of protein-protein interactions is not only a major undertaking but often requires methods that are amenable to genome-wide or targeted network analysis. The technology is highly required to analyze networks of interacting proteins encoded by the entire human genome. If high throughput transfection and monitoring systems are established, it is possible to express a target gene, to monitor the level of a gene product and to analyze the effect of the gene expression on cellular function in intact cells in real time.

The solid phase transfection technology is preferable to this purpose. In fact, J. Ziauddin and D. M. Sabatini have reported the solid phase-transfection method (Junaid Ziauddin & David M. Sabatini: Microarrays of cells expressing defined cDNAs, Nature 411, 107–110, 2001). In this paper, geratin is used to transfect DNA into cells by forming DNA-geratin complex to fuse with cell membrane. However, the method covers only a few cell lines, and has a problem for reproducibility and transfection efficiency.

Therefore, an object of the present invention is to provide a DNA array for high throughput solid-phase transfection, and a method for carrying out high throughput solid-phase transfection using the DNA array, which solve the above-mentioned problems.

DISCLOSURE OF THE INVENTION

The present invention is based on the finding that transfection efficiency is remarkably improved and cross-contamination is highly reduced in the presence of a cell-adhesion protein in dried spots printed on a surface of a solid support, which contain plasmid DNAs.

Accordingly, a solid-phase transfection method of the present invention can be carried out by the following procedures:
  (a) preparing a DNA-containing mixture comprising a plasmid DNA to be introduced into cells, a transfection reagent, and a cell-adhesion protein,
  (b) spotting the DNA-containing mixture on a surface of a solid support in a plurality of defined locations,
  (c) allowing the DNA-containing mixture to dry on the surface of the solid support,
  (d) plating cells onto the surface of the solid support, and
  (e) maintaining the solid support and the cells under appropriate conditions for transfection to proceed efficiently.

or
  (a) preparing a DNA-containing mixture comprising a plasmid DNA to be introduced into cells, and a cell-adhesion protein,
  (b) spotting the DNA-containing mixture on a surface of a solid support in a plurality of defined locations,
  (c) allowing the DNA-containing mixture to dry on the surface of the solid support,
  (d) exposing the printed solid support to the diluted transfection reagent,
  (e) plating cells onto the surface of the solid support, and
  (f) maintaining the solid support and the cells under appropriate conditions for transfection to proceed efficiently.

Further, the present invention relates to a DNA array for transfection which comprises a plurality of dried spots on a solid support, said dried spot comprises (1) a plasmid DNA to be introduced into cells, (2) a transfection reagent and (3) a cell-adhesion protein.

Still further, the present invention relates to a method for producing a DNA array, comprising:
  (a) preparing a DNA-containing mixture comprising a plasmid DNA to be introduced into cells, a transfection reagent, and a cell-adhesion protein,
  (b) spotting the DNA-containing mixture on a surface of a solid support in a plurality of defined locations,
  (c) allowing the DNA-containing mixture to dry on the surface of the solid support.

In addition, the present invention relates to a reagent kit for manufacturing the above mentioned DNA array, which comprises (1) a plasmid DNA to be introduced into cells, (2) a transfection reagent, and (3) a cell-adhesion protein.

Finally, the present invention relates to a method for gene profiling in cells, comprising:

(a) plating cells onto the surface of the above mentioned DNA array, (b) maintaining the adhered cells on plasmid under conditions appropriate for cell proliferation, (c) expressing transfected genes in cells, and (d) monitoring an exogenously produced protein and detecting changes of cellular phenotypes due to the expression of the protein.

According to the present invention, introduction of DNA into cells become highly efficient, cross-contamination detected as a signal from the neighboring places become negligible, and the solid-phase transfection system using DNA array provides high throughput transfection system. Based on the above mentioned findings, profiling a gene product expressed in cells, monitoring a change of cell phenotype, and analyzing a network of protein-protein interaction in mammalian cells become possible for the first time.

In fact, by a high throughput transfection of peptide-expression library in cells using the present invention, the present inventors have successfully identified a peptide that inhibits specific protein-protein interaction, and analysis of the network pathway using the peptide became possible.

BRIEF DESCRIPTION OF THE DRAWINGS

FIG. 1 shows the results of solid-phase transfection efficiency under different plasmid DNA (pEGFP-N1)/cationic lipid (Tfx-20) ratios. The horizontal axis shows a ratio ($\mu$g/nmol) of plasmid DNA to cationic lipid and the vertical axis shows a transfection efficiency (%), which is detected as fluorescence of Green Fluorescent Protein (GFP) and calculated by the following equation:

counts of transfected cells/counts of whole cells in a defined location×100.

FIG. 4(a) is a scheme of the array pattern. The square of 1.3 mm×1.3 mm is demarked by 0.4 mm line of hydrophobic ink. FIG. 4(b) shows HeLa cells adhered on the square. FIG. 4(c) shows Enhanced Green Fluorescent Protein (EGFP) fluorescence image of the HeLa cells of FIG. 4(b).

FIG. 5(a) is the scheme of the array pattern: Green, pEGFP was printed; red, pDsRed1 was printed. FIG. 5(b) shows HeLa cells adhered on the array. FIG. 5(c) shows EGFP/RFP image. FIG. 5(d) shows RFP image of the HeLa cells of FIG. 5(b).

FIG. 6(a) shows the results of micro-colony counts (slashed bar) and single cell counts (closed bar) on the pEGFP-pep library array. FIG. 6(b) shows the results of frequency of micro-colony in each sample. pEGFP-pep and pEGFP-p21 pep were the negative and the positive controls, respectively.

BEST MODE FOR CARRYING OUT THE INVENTION

The invention is explained in detail hereafter.

The present invention relates to the DNA array occupied by plural dried spots on a solid support, which are consisted of (1) a plasmid DNA to be introduced into cells, (2) a transfection reagent, and (3) a cell-adhesion protein.

As the solid support, there are mentioned a glass plate, a plastic plate and silicon plate etc., among which a glass plate is preferred. A glass plate may be treated by a poly L-lysine solution.

As the cell adhesion protein (3), fibronectin, pronectin, vitronectin, laminin and collagen etc. are mentioned, in which fibronectin and pronectin are preferred.

As the transfection reagents (2), a cationic lipid, a dendrimer and calcium phosphate etc. are mentioned, in which the cationic lipid and the dendrimer are preferred. The examples of cationic lipids include a polyamine based polymer such as Lipofectamine™ (Invitrogen Co., Carlsbad, Calif., USA), Transfectam™ (Promega Co., Madison, Wis., USA), Tfx™-20 (Promega Co., Madison, Wis., USA) and Effectene™ (QIAGEN Co., Valencia, Calif., USA), and a polyimine-based polymer such as Jet PEI™ (PolyPlus-transfection, Cedex, France) and ExGen™ 500 (FERMENTAS Inc., Hanover, Md., USA). They are commercially available.

The dendrimer to be used in the present invention is polyamidoamine which has dendrically ramified from the center of a molecule and has positively charged amino group at the ends to interact with negatively charged phosphate group of DNA. As the results, DNA is condensed compactly and the complex is incorporated into cells through endocytosis. Examples of a commercially available dendrimer include PolyFect™ reagent (QIAGEN) and SuperFect™ reagent (QIAGEN)

The plasmid DNA (1) to be introduced into cells comprises randomly selected cDNA and a genomic DNA harboring a coding region in an expression vector. Preferred examples include a plasmid to overexpress a gene and a plasmid to knockout a gene. In addition, the plasmid DNA (1) may include a reporter gene encoding a marker protein. Examples of the marker proteins are Enhanced Green Fluorescent Protein (EGFP), Red Fluorescent Protein (RFP), Luciferase, Secreated alkaline phosphatase (SEAP) and β-galactosidase, in which EGFP and RFP are desirable. Commercially available plasmid-based vectors, such as pEGFP (Clontech), pDsRed2 (Clontech), pTimer (Clontech) etc. can be used.

Dried spots on the solid support can be obtained by spotting the mixture of (1) a plasmid DNA to be introduced into cells, (2) a tansfection reagent and (3) a cell-adhesion protein onto a solid support and by allowing the spotted mixture to dry in air or in vacuo on the surface of the solid support.

Size and shape of the spots are not specifically limited. For example, a diameter of the spots may be from about 0.01 to about 5 mm and a shape of the spot viewed from the above is possibly a circle. Thickness of the dried spots is not specifically limited, and a range of the thickness may be from about 1 to about 100 $\mu$m.

Number of the spots is not specifically limited, and it may be from about 1 to about 10,000 pieces. It is preferable that each spot contains a different kind of genes in an expression vectors. Each spot is preferably isolated from neighbored spots, for example, by dividing each spot by hydrophobic lines such as Teflon. Each dried spot preferably contains (1) a plasmid DNA to be introduced into cells from about 100 pg/mm$^2$ to about 1 μg/mm$^2$, preferably from about 2 to about 200 ng/mm$^2$, (2) a transfection reagent from about 0.01 to about 10 μg/mm$^2$, preferably from 0.1 to 1 μg/mm$^2$, (3) a cell-adhesion protein from about 0.01 to about 10 μg/mm$^2$, preferably from 0.1 to about 1 μg/mm$^2$.

The DNA array of the present invention is obtained by preparing a DNA-containing mixture comprising plasmid DNA to be introduced into cells, a transfection reagent, and a cell-adhesion protein, spotting the DNA-containing mixture on a surface of a solid support in a plurality of defined locations, allowing the DNA-containing mixture to dry on the surface of the solid support, whereby the plasmid DNA containing mixture affixed to the surface in plural defined discrete locations.

The plasmid DNA to be introduced into cells is prepared, for example, from recombinant *Escherichia coli* cells. The cell-adhesion protein is, for example, prepared by extraction and purification of recombinant *E. coli* cells or human/porcine tissues. As the transfection reagent, the above mentioned commercially available products can be used.

A concentration of the plasmid DNA in the DNA-containing mixture is from about 0.01 to about 5 μg/μl, preferably from about 0.05 to about 0.5 μg/μl. A concentration of the transfection reagent in the DNA-containing mixture is from about 0.01 to about 20 μg/μl preferably from 0.1 to 1 μg/μl. Further, a concentration of the cell-adhesion protein in the DNA-containing mixture is from about 0.01 to about 5 μg/μl, preferably from 0.1 to 1 μg/μl.

The preparation of dried spots from the above mentioned DNA-mixture is carried out by spotting on the surface of a solid support using ink-jet type spotter or pin-array type spotter followed by drying in air or in vacuo.

In the solid-phase transfection method of the present invention, after preparing the DNA array as in the above, supply of cells on the surface of the DNA array is carried out by plating cells thereon. The number of cells supplied onto one dried spot is dependent on cell type, preferably about 1 to 10,000, more preferably about 50 to 1,000.

Cells supplied onto the dried spots of the DNA array are adhered on the surface of each spot with the aid of adhesion protein, and then, plasmid DNAs affixed to the surface of the solid support enter cells under the conditions appropriate for transfection to occur.

The solid-phase transfection method of the present invention is characterized in that it can minimize cross-contamination among the spots, because the cell-adhesion proteins in the spots help cells to be anchored onto the spot.

Furthermore, the present invention relates to the method for gene profiling, which comprises plating cells on the surface of the printed solid support, introducing plasmid DNA into cells maintaining the solid support in the appropriate conditions for transfection to occur, expressing the gene inserted to the expression vector in cells, and detecting the protein in transfected cells, or monitoring a cell phenotype derived from transfected cells.

In the gene profiling of the present invention, the level of proteins expressed in cells are monitored by a desired wavelength using fluorescent microscope. For example, enhanced green fluorescent protein and red fluorescence protein are maximally excited at 488 and 558 nm followed by detecting at 509 and 583 nm of maximal fluorescent wavelength, respectively. In the meanwhile, to monitor the cell phenotype derived from transfected cells, for example, cell death is detected under the observation using phase contrast microscope and nuclear staining with propiodium iodide.

In the gene profiling of the present invention, for example, screening of peptide is carried out by monitoring cell death during expression of a gene to suppress the gene products essential for cell proliferation. For example, expression of a peptide library encoding a part of the target gene is applicable for suppressing a specific function of a gene product.

EXAMPLES

In the following, the present invention is explained in more detail by referring to Examples, but the scope of the present invention is not limited to them.

Example 1

The representative example of the transfection reagent is cationic lipids, which include Tfx™-20 (Promega, Madison, Wis., USA), and Effectene™ (QIAGEN, Valencia, Calif., USA). Both transfection reagents condense and wrap plasmid DNAs in cationic lipids. The complex of plasmid DNA and transfection reagent is fused with cell membrane and then plasmid DNA is entered inside cells.

The glass plate was prepared as follows: The glass slides (7 cm×2.5 cm) were marked with 80 squares (2 mm×2 mm) distincted by 1-mm Teflon line. The glass slides were treated by incubation for 1 hr in ammonium hydroxide solution (Aldrich, Milwaukee, Wis., USA) and washed with distilled water. Then, the glass plates were incubated in poly-L-Lysine solution (10% (v/v) poly-L-lysine solution (Sigma, St. Louis, Mo., USA) and 10% (v/v) phosphate buffered saline buffer) for 1 hr and washed with distilled water. The glass plates were air dried and stored in a desiccator until use.

Plasmid samples (pEGFP-N1; Clontech, U.S. Palo Alto, Calif.) of 1 μl (0.5 μg/μl in distilled water) were spotted on the glass plates. Plasmids were printed by drying at room temperature. For DNA/cationic lipid complex formation, the printed DNA samples were exposed to the diluted solution of Tfx™-20 transfection reagent for 5 min at room temperature just before transfection. The diluted solution of Tfx™-20 transfection reagent contained 100 μM of N,N,N',N'-tetramethyl-N,N'-bis(2-hydroxyethyl)-2,3-di(oleo yloxy)-1,4-butanediammonium iodide.

Cells of 7×10$^5$ were suspended into 25 ml DMEM preheated at 37° C. The cell suspension was poured into each 100-mm tissue culture dish in which the DNA-printed glass plate was placed. The cells were incubated for 72 hr at 37° C. in humidified 5% CO$_2$ atmosphere. Fluorescent microscopic images of EGFP-expressed cells on the glass plates were taken by an optical camera system (Zeiss). Transfection efficiency was calculated by the equation: transfection efficiency=counts of transfected cells/counts of whole cells× 100 (%). Transfected and whole cells in the photographic images were counted manually and used in the calculation. Cross-contamination frequency on each glass plate was calculated according to the equation: Cross-contamination frequency (%)=(Counts of transfected cells on the square without printed DNA/counts of transfected cells on the adjacent square containing printed DNA)×100 (%). The frequency was evaluated by using average value in 8 measurements.

Figure 1:
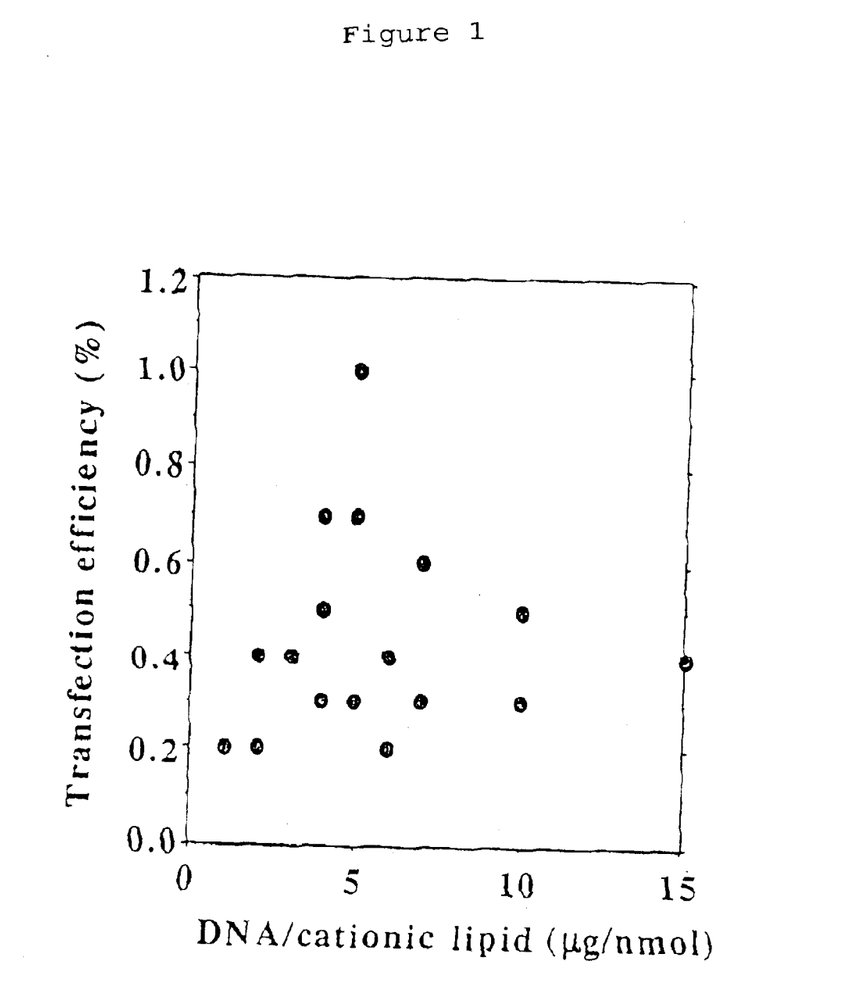

The solid-phase transfection efficiency was found to be sensitive to DNA/cationic lipid ratio (FIG. 1). The transfection efficiency was improved by increasing the DNA to cationic lipid ratio up to 5 μg DNA/nmol cationic lipid. Addition of excess amounts of cationic lipid inhibited adherence and growth of HeLa cells, resulting in a decreased level of transfection efficiency. Absolute concentration of DNA/ cationic lipid per given surface area also affected the transfection efficiency of HeLa cells. The maximal transfection efficiency was obtained at DNA concentration of 0.13 $\mu g/mm^2$. The lower concentration of DNA reduced the transfection efficiency. DNA concentrations of more than 0.13 $\mu g/mm^2$ inhibited cell adherence and growth due to the presence of excess amount of cationic lipid on the grid. The highest transfection efficiency by using the optimized protocol described above was 5% (Table 1). However, the average cross-contamination frequency was 44% (Table 1).

TABLE 1

| Mediators | Maximal efficiency (%) | Average cross-contamination (%) |
| --- | --- | --- |
| Tfx-20 (liposome) | 5 | 44 |
| Effectene (liposome) | 2 | 33 |
| Effectene + Fibronectin | 32 | 5 |
| PolyFect (dendrimer) | 3 | 28 |
| PolyFect + Fibronectin | 36 | 1 |

Next, pEGFP-N1 (60 ng/$\mu$l) was printed on the poly-L-lysine coated glass slide. At the same time, the glass slide printed with both pEGFP-N1 (60 ng/$\mu$l) and human fibronectin (0.8 $\mu$g/$\mu$l, Nakarai, Tokyo, Japan) were prepared for comparison. The printed DNA samples were exposed to the mixture containing 300 $\mu$l of EC buffer, 16 $\mu$l of Enhancer and 60 $\mu$l of Effectene transfection reagent (QIAGEN Co). HeLa cell suspension was plated onto the slide glass, and then, the fluorescence of EGFP in transfected cells was monitored after incubation for 72 hr. Although the transfection efficiency is 2% and the cross-contamination was 40% in the spot containing pEGFP-N1 alone, the former increased to 32% and the latter was decreased to 5% in the spot containing both pEGFP-N1 and fibronectin (Table 1 shows the comparison of solid-phase transfection systems using Tfx-20 cathionic lipid (liposome), Tfx-20+Fibronectin, Polyfect (dendrimer), and Polyfect+Fibronectin as mediators.). The addition of fibronectin to the DNA was highly efficient to increase transfection efficiency and to minimize cross-contamination.

Example 2

PolyFect™ transfection reagent (QIAGEN Co.) is consisted of an active dendrimer molecules which is diverged from a center of the molecule and have positively charged amino groups at the branched termini to interact with phosphate groups of DNA. PolyFect™ reagent makes DNA to condense in compact form which is easily incorporated into cells by endocytosis.

Figure 2:
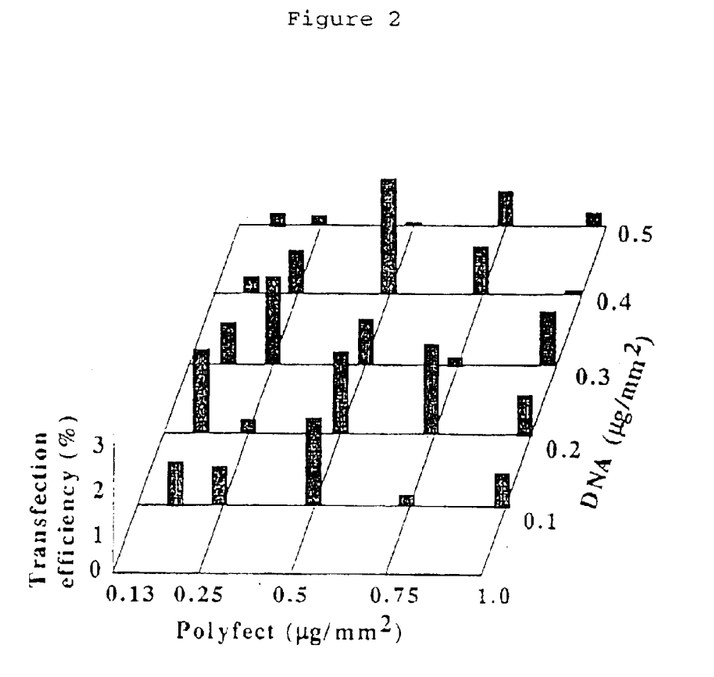
FIG. 2 shows the results of transfection efficiency at different concentrations and ratios of plasmid DNA and dendrimer.

DNA/PolyFect ratio in the DNA printing mixture (minus fibronectin) was investigated to obtain the highest transfection efficiency (FIG. 2). Inhibition of adherence and growth of HeLa cells was observed at concentrations of PolyFect in excess of 1.0 $\mu g/mm^2$. At 0.5 $\mu g/mm^2$ of PolyFect, relatively high transfection efficiency was observed using 0.1 to 0.4 $\mu g/mm^2$ DNA. Larger or lower concentrations of PolyFect resulted in relatively low transfection efficiency probably due to the presence of excess charge on the surface and/or the non-optimal particle size of DNA/dendrimer complex for of HeLa cell transfection. The maximal transfection efficiency was 3% in the range of the optimal DNA/PolyFect ratio (Table 1). However, the average cross-contamination frequency was at an unacceptable level of 28% (Table 1).

Figure 3:
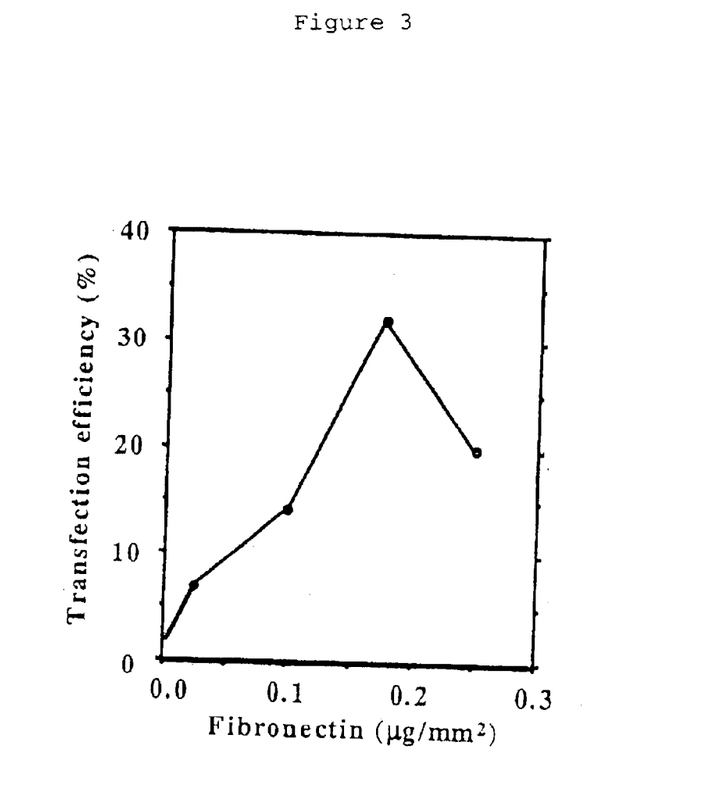
FIG. 3 shows the results for the effect of fibronectin on the transfection efficiency of dendrimer-mediated solid-phase transfection.

The efficiency of dendrimer-mediated solid-phase transfection was dramatically increased by the addition of fibronectin (FIG. 3). The addition of fibronectin also virtually eliminated the cross-contamination frequency. The average frequency of cross-contamination at 0.25 $\mu g/mm^2$ of fibronectin was 1% (Table 1). The effect of fibronectin on the transfection efficiency and cross-contamination frequency most likely results from acceleration of adherence of HeLa cells, since fibronectin is an epithelial cell attachment factor.

Example 3

The DNA printing and complex formation procedures for cationic lipid and dendrimer-mediated solid-phase transfection systems are different. In the cationic lipid-mediated solid-phase transfection procedure, DNA was printed first, then, the DNA/cationic lipid complex was formed on the solid glass support. The physical process of exposing DNA to cationic lipids most likely increased the chance of cross-contamination of DNA between adjacent grid locations.

On the contrary, in the case of the dendrimer-mediated solid-phase transfection, DNA/dendrimer complex is directly printed on the glass plates. This is a simpler process than the cationic lipid-mediated system and reduced the chance of cross-contamination. In fact, the average frequency of cross-contamination in the dendrimer-mediated system was lower than the cationic lipid-mediated system (Table 1). The results suggest that the dendrimer-mediated system is well-suited for high-throughput transfection system. The use of fibronectin for dendrimer-mediated system allows the design of a high density DNA array for use in high-throughput solid-phase transfections.

Example 4

Figure 4:
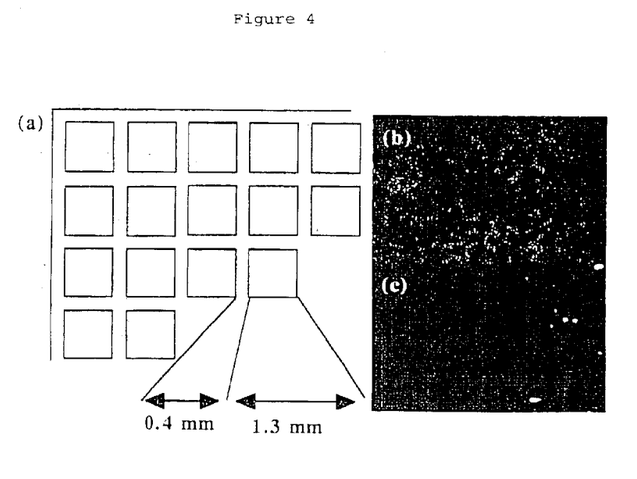
FIG. 4 shows the results of dendrimer-mediated solid-phase transfection on a compact array.

A compact DNA array was developed based on the dendrimer/fibronectin-mediated solid-phase transfection system (FIG. 4). The density of the pattern allows to print 800 plasmid samples on a slide glass (7 cm×2.5 cm). It should be noted that two fold higher density will not afford statistically significant number of adhered and/or transformed cells per grid to be useful in genetic selection studies. 0.5 $\mu$l of the DNA printing mixture, which contained 40 ng pEGFP-pep (details are described in Example 5), 0.2 $\mu$g fibronectin, was spotted in each square. After plating HeLa cells onto the slide glass, 25 $\mu$l of gene expression inducer (2 mg/ml doxycycline) was added into the cell suspension. The cells adhered on the glass plate very well (FIG. 4. (b)). Transfected cells expressed EGFP were observed in the area that DNA was printed (FIG. 4. (c)). The transfection efficiency was 10.5%.

Figure 5:
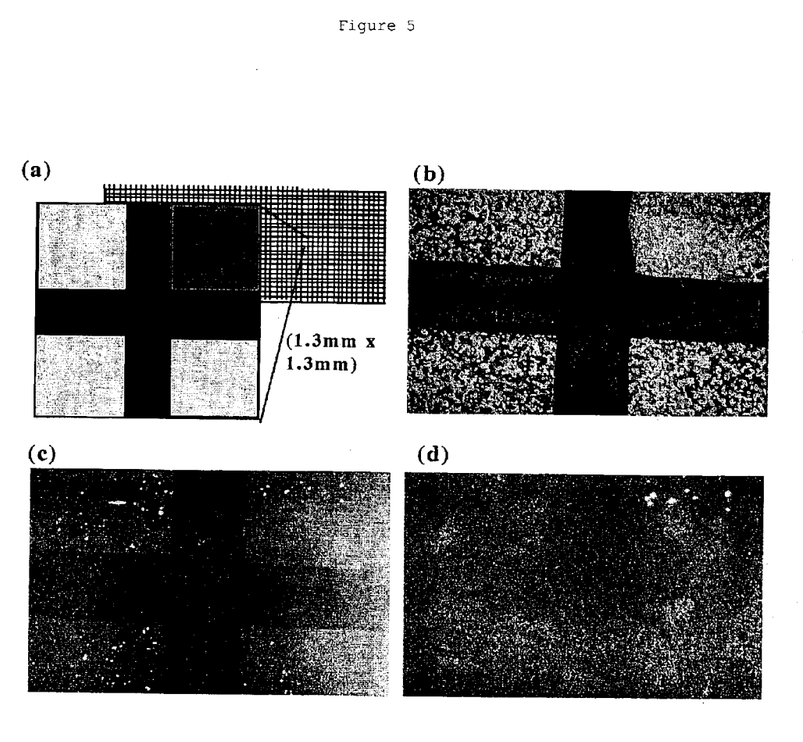
FIG. 5 shows the results of the genetic selection of Red Fluorescent Protein (RFP) expression vector on a compact transfection array system based on the dendrimer-mediated solid-phase transfection.

Cross-contamination of the compact array system was examined by using EGFP expression vector (pEGFP-N1) and a red fluorescent protein (RFP) expression vector (pDsRed1 vector, Clontech, Palo Alto Calif.) (FIG. 5). The DNA printing mixtures of PEGFP and pDsRed1 optimized for the compact array were spotted as shown in FIG. 5(a). As shown in FIG. 5(b), HeLa cells adhered on the glass surface and the hydrophobic lines demarking the grids. EGFP expressed cells were frequently observed in the squares on which the pEGFP was printed (FIG. 5(c)). RFP expressed cells were observed only in the squares on which the pDsRed1 was printed (FIG. 5. (d)). In the sets of experiment, there were no cross-contamination between EGFP expressed cells and RFP expressed cells. The demonstration indicates that the dendrimer-mediated solid-phase transfection developed for the compact array system can be applied for accurate genetic selection.

Example 5

Figure 6:
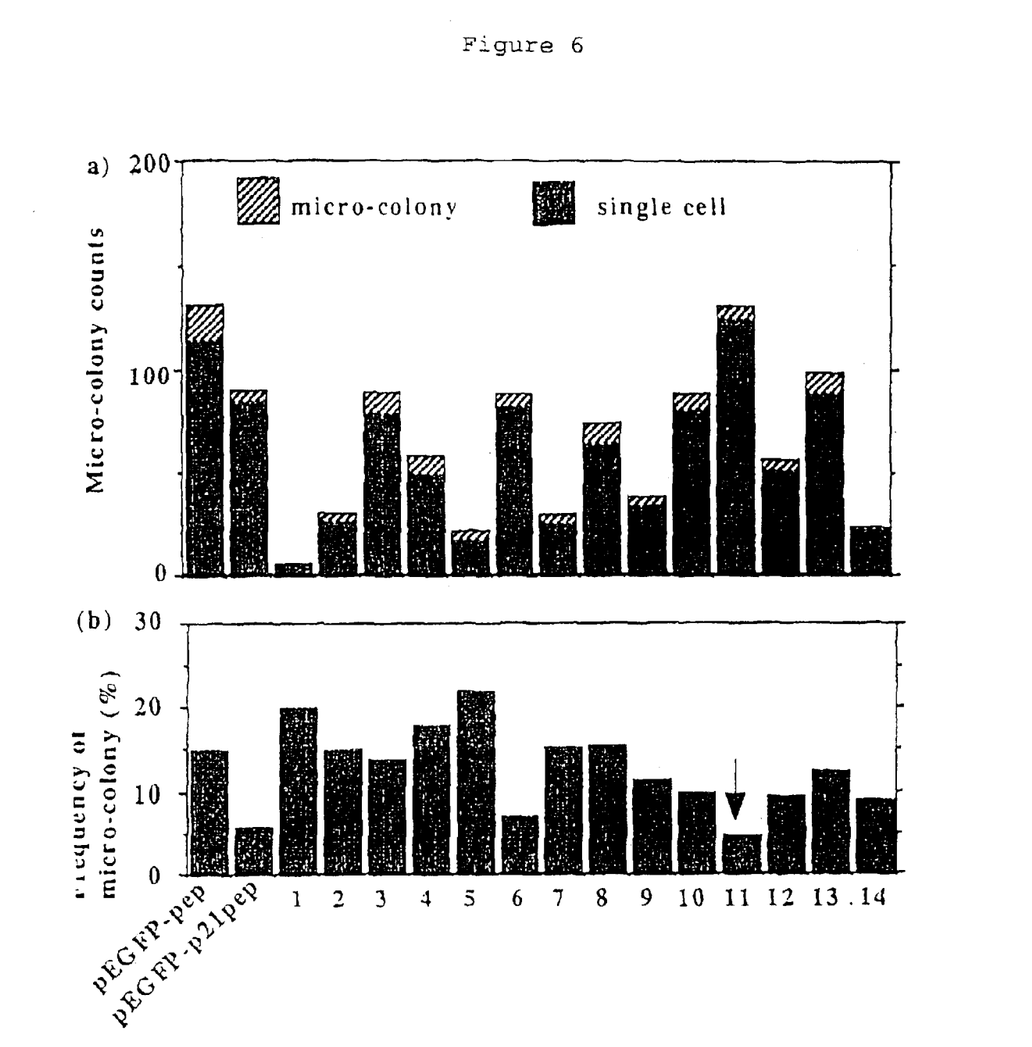
FIG. 6 shows the results of genetic selection of proliferative inhibitor peptides by using the dendrimer-mediated solid-phase transfectin system.

The pTRE2 vector (Clontech Col.) contains the CMV promoter together with TRE (tetracycline response element)

in which the addition of either doxycyclin or tetracycline is required for a gene expression under the control of the CMV promoter. Peptide-EGFP fused protein expression vector, pEGFP-pep was constructed by ligation of the 3.8 kb fragment of pTRE2 digested with XbaI with 0.8 kb fragment encoding EGFP prepared by digestion with XbaI. Plasmids coding randomized peptide EGFP fusion proteins were prepared based on primer extension methods: template DNAs (5'-AACCGCGGATGTGTAACGGCGGCAG ACCAGCGCTACAGATTTCTACCACTCCARRARR RRDTADTATWTTCCTGCGGATCGATAAA-3' (SEQ ID NO: 1)) were denatured at 94° C. for 10 mm and annealed with primer DNA (5'-TTTATCGATCCGCA-3' (SEQ ID NO: 2)) in TE buffer at 4° C. overnight. Primer extension reaction of the annealed DNA samples was carried out at 37° C. for 30 min in the presence of 10 µg/ml DNAs, 100 units/ml Kienow fragment (New England Biolabs, Beverly, Mass., USA), 10 mM Tris-HCl (pH 7.5), 5 mM $MgCl_2$, 7.5 mm dithiothreitol. The reaction products were digested by SacII and ClaI, then purified by QIAquick PCR purification kit (QIAGEN, Valencia, Calif., USA). The SacII-ClaI fragments were cloned into the SacII-ClaI site in pEGFP-pep. The plasmids cloned in *Escherichia coli* XL1-blue were purified by QIAprep kit (QIAGEN, Valencia, Calif., USA) and eluted by distilled water from the QIAprep columns. Concentration of each plasmid solution was adjusted to 0.5 µg/µl for cationic lipid-mediated transfection and 0.2 µg/µl for dendrimer-mediated transfection by dilution with distilled water and was used for solid-phase transfection experiments. The biased plasmid library constructed here encodes CDK-cyclifle binding peptide derivatives designed from p21waf1/ciP1 G1 cell cycle checkpoint protein (Toyashima, H. and Hunter T.: Cell, 78, 67–74, 1994) . The plasmid library was printed on a glass plate (80 squares, 2 mm×2 mm) FIG. 6 shows the example results of the genetic selection of proliferative inhibitor peptides from 14 plasmids. After the solid-phase transfection as shown in Example 4, the cells were fixed by exposing to paraformaldehyde solution (4% in PBS buffer) for 15 min at room temperature. Then the cells were exposed to 0.5% Triton X-100 for 30 sec and were washed twice with PBS buffer. For image-based selection, the cells were stained with propidium iodide (PI) by exposing to PI solution (20 µg/ml PI, 200 µg ribonuclease A per 1 ml of PBS buffer) for 30 min at room temperature. In the EGFP expressed cells, microcolony, which is defined as duplicating cell (including S, M and G2 phase), and G1 cells were counted manually. The number of transfected cells was variable in each square (FIG. 6*a*) probably due to small differences in the DNA printing conditions. However, the frequency of microcolony on the pEGFP-pep printed area was 15% and the frequencies of micro-colony on the areas printed with negative peptide coding vectors were within the range of 10–20% (FIG. 6*b*). However, the frequency on the positive peptide-coding vector (#11) was 5% and was similar to the observed 6% frequency of the positive control grid (pEGFP-p21 pep). These examples indicate that the transfected cells on the array changed their phenotypes by the effect of expressed peptides. The above proof of principle study suggests that the transfection array system is a novel and powerful tool for high-throughput genetic selection with mammalian cells.

INDUSTRIAL APPLICABILITY

The present invention is applicable for a gene network analysis which is the most important subject in post-genome sequencing period. If the data base of the gene network is constructed once, the value is extremely high based on the application to drug discovery, medicare, diagnostics and food industry. In addition, the contracted service based on gene network data base is highly possible.

The present invention can be used to identify aptamers or peptides which inhibit protein-protein interaction specifically. They may be possible candidates for medicine, diagnostic reagent or reagent for research tool. Especially, either peptide-mimetics or low molecular weight compounds may be synthesized based on the sequence of the peptide, which will be a candidate for a drug to cure or prevent disease.

In addition, the present invention provides a novel tool to find a new target for drug discovery.

What is claimed is:

1. A DNA array for transfection which comprises a plurality at dried spots on a solid support, said dried spots comprising (1) a plasmid DNA to be introduced into cells, (2) a transfection reagent and (3) a cell-adhesion protein.

2. The DNA array of claim 1, wherein (3) the cell-adhesion protein is fibronectin.

3. The DNA array of claim 1, wherein (2) the transfection reagent is selected from the group consisting of a cationic lipid and a dendrimer.

4. The DNA array of claim 1, wherein (1) the plasmid DNA to be introduced into cells further comprises a reporter gene.

5. A method for producing the DNA array of claim 1 comprising:
   (d) preparing a DNA-containing mixture comprising a plasmid DNA to be introduced into cells, a transfection reagent, and a cell-adhesion protein,
   (e) spotting the DNA-containing mixture on a surface of a solid support in a plurality of defined locations,
   (f) allowing the DNA-containing mixture to dry on the surface of the solid support.

6. A reagent kit for manufacturing the DNA array of claim 1, which comprises (1) a plasmid DNA to be introduced into cells, (2) a transfection reagent, and (3) a cell-adhesion protein.

7. A solid-phase transfection method comprising:
   (a) plating cells onto the surface of the DNA array of claim 1, and
   (b) maintaining the DNA array and the cells under appropriate conditions for transfection to proceed efficiently.

8. A solid-phase transfection method comprising:
   (a) preparing a DNA-containing mixture comprising a plasmid DNA to be introduced into cells, a transfection reagent, and a cell-adhesion protein,
   b) spotting the DNA-containing mixture on a surface of a solid support in a plurality of defined locations,
   (c) allowing the DNA-containing mixture to dry on the surface of the solid support,
   (d) plating cells onto the surface of the solid support, and
   (e) maintaining the solid support and the cells under appropriate conditions for transfection to proceed efficiently.

9. The solid-phase transfection method of claim 8, wherein the cell-adhesion protein is fibronectin.

10. The solid-phase transfection method of claim 9, wherein the transfection reagent is a dendrimer.

11. A solid-phase transfection method comprising:
   (a) preparing a DNA-containing mixture comprising a plasmid DNA to be introduced into cells and a cell-adhesion protein selected from the group consisting of: fibronectin, pronectin, vitronectin, laminin, and collagen,
   (b) spotting the DNA-containing mixture on a surface of a solid support in a plurality of defined locations,
   (c) allowing the DNA-containing mixture to dry on the surface of the solid support,
   (d) exposing the dried DNA-containing mixture of step (c) to a solution containing a transfection reagent,
   (e) plating cells onto the surface of the solid support, and
   (f) maintaining the solid support and the cells under appropriate conditions for transfection to proceed efficiently.

12. The solid-phase transfection method of claim 11, wherein the cell-adhesion protein is fibronectin.

13. The solid-phase transfection method of claim 12, wherein the transfection reagent is a cationic lipid.

14. A method for gene profiling in cells, comprising:
   (a) plating cells onto the surface of the DNA array of claim 1,
   (b) maintaining the adhered cells on plasmid under conditions appropriate for cell proliferation,
   (c) expressing transfected genes in cells, and
   (d) monitoring an exogenously produced protein and detecting changes of cellular phenotypes due to the expression of the protein.

15. The method of claim 8 further comprising the step of a network analysis, screening of seed compounds for drug discovery, or detection of a novel diagnostic marker.

16. An article of manufacture comprising a transfection reagent in a container and a DNA array for transfection which comprises a plurality of dried spots on a solid support, said dried spots comprising a plasmid DNA to be introduced into cells and a cell-adhesion protein.

17. The article of manufacture of claim 16, wherein the cell-adhesion protein is selected from the group consisting of fibronectin, pronectin, vitronectin, laminin, and collagen.

18. The article of manufacture of claim 16, wherein the cell-adhesion protein comprises fibronectin.

19. The article of manufacture of claim 17, wherein the transfection reagent is selected from the group consisting of a cationic lipid and a dendrimer.

20. The article of manufacture of claim 17, wherein the plasmid DNA further comprises a reporter gene.

* * * * *

SEQUENCE LISTING

```
<160> NUMBER OF SEQ ID NOS: 2

<210> SEQ ID NO 1
<211> LENGTH: 89
<212> TYPE: DNA
<213> ORGANISM: Artificial Sequence
<220> FEATURE:
<223> OTHER INFORMATION: Synthesized

<400> SEQUENCE: 1
aaaccgcgga tgtgtaaacg gcggcagacc agcgctacag atttctacca ctccarrarr      60
arrdtadtat wttcctgcgg atcgataaa                                        89

<210> SEQ ID NO 2
<211> LENGTH: 14
<212> TYPE: DNA
<213> ORGANISM: Artificial Sequence
<220> FEATURE:
<223> OTHER INFORMATION: Synthesized
```

```
<400> SEQUENCE: 2
tttatcgatc cgca                                                        14
```